United States Patent [19]

Reich

[11] Patent Number: 4,973,466
[45] Date of Patent: Nov. 27, 1990

[54] WOUND-HEALING DRESSINGS AND METHODS

[75] Inventor: Cary Reich, Laguna Hills, Calif.

[73] Assignee: Chiron Ophthalmics, Inc., Irvine, Calif.

[21] Appl. No.: 209,310

[22] Filed: Jun. 21, 1988

[51] Int. Cl.$^5$ .................. A61K 9/70; A61K 37/02
[52] U.S. Cl. .................... 424/426; 424/428; 424/429; 514/2; 514/21; 514/953; 514/954; 514/944
[58] Field of Search ............ 514/2, 21, 953, 954, 514/944; 424/426, 428, 429

[56] References Cited

U.S. PATENT DOCUMENTS

| | | | |
|---|---|---|---|
| 4,377,572 | 3/1983 | Schwarz et al. | 514/21 |
| 4,453,939 | 6/1984 | Zimmerman et al. | 604/304 |
| 4,683,142 | 7/1987 | Zimmermann et al. | 427/2 |
| 4,727,059 | 2/1988 | Binder et al. | 514/8 |
| 4,740,498 | 4/1988 | Hirao et al. | 514/21 |
| 4,784,989 | 11/1988 | Hook et al. | 514/2 |

OTHER PUBLICATIONS

Caffesse et al., "The effect of citric acid and fibronectin application on healing ... " BA 80(11):93485, 1985.
Nishida et al., "Fibronectin enhancement of corneal epithelial wound healing of rabbits in vivo" BA 78(2):15426, 1984.
Fujikawa et al., "Fibronectin in healing rabbit corneal wounds" BA 73(3):21245.

Primary Examiner—Jacqueline Stone
Assistant Examiner—Jean C. Witz
Attorney, Agent, or Firm—Bernard, Rothwell & Brown

[57] ABSTRACT

Wound healing dressings are prepared by flocculating fibronectin, a biologically active fragment or an analog thereof to produce a water-swellable gel. The gels, in the form of sheets, strips, wedges, strands or I-shaped cross-sections, are especially useful in promoting the healing of corneal, scleral dermal, incisional wounds or lesions. They can be used to enhance the results obtained in keratorefractive surgeries and the healing scleral incision for intraocular surgery.

14 Claims, No Drawings

WOUND-HEALING DRESSINGS AND METHODS

BACKGROUND OF THE INVENTION

This invention relates to wound-healing dressings and to methods for enhancing the quality of wound healing. In particular, the invention relates to the healing of corneal wounds. In one embodiment, the invention relates to methods and materials for improving the results obtainable in keratorefractive surgeries, such as radial keratotomy, by altering the course of healing of the surgical incisions. In another embodiment, the invention relates to the sutureless closing of tears or perforations of the cornea, limbus, sclera and all oculoplasty.

As used herein, the term "wound" includes surgical incisions as well as wounds caused by accidental trauma or disease. A considerable body of literature is devoted to methods for improving wound-healing, both in terms of increasing rates of healing and avoiding undesirable effects associated with natural wound-healing processes, such as scarring and contraction of healed tissue. Not only are those effects undesirable from a cosmetic point of view, but also, in the case of corneal wounds, they can interfere with visual function.

U.S. Pat. No. 4,453,939 to Zimmerman et al. discloses a composition and its use for sealing and healing of wounds. The composition comprises a collagen carrier which is coated on one or all faces with a mixture of a fibrinogen component which contains fibrinogen, factor XIII-containing fibrinogen or a mixture thereof, and a thrombin component. It is said that the mixture may contain additives, such as fibronectin which promote the infiltration and growth of fibroblasts. Those skilled in the art are aware that the deposition of collagenous materials into a wound bed may have undesirable effects in wound healing, since crosslinking of collagen during the healing process tends to cause tissue shrinkage and scarring. These effects are particularly undesirable in ophthalmological applications, where scarring and shrinkage may impair vision. U.S. Pat. No. 4,444,787 describes the treatment of wounded ocular tissue by the topical application of collagen crosslinking inhibitors to the tissue. Application of the crosslinking inhibitor is said to reduce shrinkage of collagen fibers located in ocular tissue.

A number of publications describe the use of tissue adhesives to bind wound surfaces following accidental corneal perforations or corneal surgery. These include: *Ophthalmic Surg.*, 15(1):55-57 (1984); *Aust. J. Ophtalmol.*, 11(2):113-118 (1983); *Opthalmology*, 89(6):630-635 (1982); *Ophthalmic Surg.*, 13(6):475-477 (1982); *Opthalmic Surg.*, 10(3): 58-64 (1979); *J. Biomed. Mater. Res.*, 5(1):113-119 (1972); *Trans. Pac. Coast Ophthalmol. Soc.*, 50:12-125 (1969); *Trans. Am. Acad. Ophthalmol. Otolaryngol.*, 73(3):499-505 (1969). The most commonly employed adhesives for use in healing wounds of the eye are cyanoacrylate type adhesives.

An adhesive of choice for treating corneal perforations is currently cyanoacrylate. Disadvantages of cyanoacrylate are that the perforation has to be completely dry before application; the polymerized glue may present brittle edges that further irritate the eye; and the glue is not sterile and is not readily available in an acceptable delivery system for the sterile field.

Wound healing in keratorefractive surgeries, such as radial keratotomies, presents an entirely different set of problems and objectives by comparison with the healing of traumatic wounds, such as corneal perforations. In the case of traumatic wounds, such as corneal tears or perforations, the desired objective is to restore the wounded tissue as nearly as possible to its original configuration. In keratorefractive surgeries, however, incisions are made into the cornea for the specific purpose of permanently changing the geometry of the cornea. Restoration of the tissues to their original configuration, therefore, would tend to reverse the desired effects of the surgery.

Keratorefractive surgeries are intended to correct vision problems caused by defects in the geometry of the eye by surgically altering the corneal geometry. Radial keratotomy is a keratorefractive surgical procedure which is employed to correct myopia caused by excessive corneal curvature. In this technique, a series of incisions is made in the cornea, usually penetrating about 90 to 95% of the thickness of the cornea. The incisions, extend along lines which radiate outwardly from the corneal center. The number of incisions may vary from as few as four to as many as 16, with 8 to 12 being commonly employed. The incisions allow the cornea to relax and to flatten out somewhat, thereby reducing or eliminating nearsightedness. Similar procedures, in which corneal incisions are made in directions other than radial directions, have been employed to correct some astigmatisms.

While radial keratotomy and related keratorefractive surgeries have become fairly commonplace, the results achieved using presently available techniques are not highly predictable or controllable in any given patient. In particular, the degree of correction is not well controlled and may be more or less than is needed by the particular individual, so that the operation may have to be repeated or corrective lenses may still be needed. Furthermore, the healing process usually takes from 12 to 24 months, during which time some patients experience instability in visual acuity; that is, the cornea begins to reacquire some of the curvature lost as a result of the operation. Maximum flattening of the cornea usually occurs about 2 days after surgery, with a gradual increase in curvature occurring thereafter until the incisions have healed.

Some keratotomy patients have also encountered postoperative vision problems related to scarring. In some instances, scars at the healed incision sites cause light to be reflected within the eye, resulting in a perceived glare, particularly at night. Fluctuations in visual acuity throughout the day may also result.

It would be highly desirable to develop methods for maximizing the degree of corneal flattening obtainable in radial keratotomies as well as providing for a predictable degree of vision correction. Furthermore, it would be desirable to enhance the quality of healing of radial keratotomy incisions so that scarring would be minimized and to increase the rate at which healing occurs.

SUMMARY OF THE INVENTION

The present invention provides wound-healing dressings, which can be formed into sheets, strips, wedges, I-shaped cross-sections or any other shape which may be useful for the particular wound-healing application at hand. The wound-healing dressing of the invention generally comprises a water-swellable gel which is prepared from fibronectin or a biologically active fragment or an analog thereof. In a preferred embodiment, the gel is prepared from fibronectin, a biologically active fragment or an analog thereof, and albumin.

The protein provides a matrix for cell growth and migration and for the deposition of wound-healing substances. Additionally, the gel becomes tacky upon contact with tissue fluids and acts as a tissue adhesive. The wound-healing dressings can be employed as wound coverings to promote healing and/or as tissue adhesives to provide closures for wounded tissues, which closures can be sutureless. The gel, in the form of an appropriately configured plug or wedge, can be inserted into a puncture, incision, tear or similar break in human or animal tissue. Due to its water-swellable nature, it immediately takes up fluid from surrounding tissues and expands to fill in the space in the wound, where it acts as a tissue adhesive and promotes healing.

Preferred applications for the wound-healing dressings of the invention are in the field of ophthalmology, particularly in the treatment of traumatic injuries, disease-induced irregularities, and surgical incisions of the cornea or sclera. In the case of a break in the corneal or scleral surface or a corneal or sclera perforation due to trauma or disease, an appropriately shaped plug or wedge of the crosslinked gel can be inserted into the break in the previously described manner. In one embodiment of the invention, the wound-healing dressing is employed to improve the results obtainable in keratorefractive surgeries such as radial keratotomy. The gel, in an appropriate configuration, is inserted into the keratorefractive incisions, where it serves not only to promote wound healing within the incision, but also to act as a spacer which maintains the desired separation of the wound margins of the incision during healing, thereby maximizing the degree of corneal flattening obtained.

The wound-healing dressings of the invention can also be employed as delivery systems for medicaments by dispersing a medicament such as an antibiotic, antimicrobial agent, antiviral agent, antiimflammatory agent, anti-protease agent, hormone, vitamin, analgesic, chelating agent, mitogenic agent, mixtures thereof or other therapeutic material within the gel. For example, a sheet of gel having an antibiotic dispersed therein can be employed as a wound covering.

There is also provided by this invention a method for producing a wound-healing dressing. The method comprises reacting a solution of fibronectin, a biologically active fragment or analog thereof with an agent capable of changing the pH or osmolarity of the solution so as to form a flocculent; recovering the flocculent from the reaction medium; and forming the flocculent to the desired shape of the dressing.

DETAILED DESCRIPTION OF THE PREFERRED EMBODIMENTS

The gel which forms the wound-healing dressing of the invention is prepared by reacting a solution of fibronectin, a biologically active fragment or an analog thereof and, optionally, one or more other proteins such as albumin, with an agent capable of changing the pH or osmolarity of the solution so as to form a flocculent. Fibronectin is a glycoprotein (4–5% carbohydrate) having a molecular weight of about 220,000 daltons, which exists in the form of a 440,000-dalton dimer. Fibronectin exists in a plasma-associated form and a cell-associated form. It can conveniently be isolated from plasma by the procedure described by Nishida et al., *Jap. J. Ophth.*, 26:4416-24 (1985). Fibronectin is also known by various other names, including cold-insoluble globulin, surface fibroblast antigen, cell surface protein, band 1, L1 band, band I, zeta-protein, major fibroblast glycoprotein, galactoprotein A, large external transformation sensitive protein (LETS), micro-fibrillar protein, cell attachment protein, cell adhesive factor, anti-gelatin factor, cell-spreading factor and opsonic factor. For a review of the structure and activities of fibronectin, see Pearlstein et al., *Mol. & Cell. Biochem.*, 29:103-125 (1980). There can also be employed, in the practice of the invention, biologically active fragments or analogs of fibronectin. For example, proteins having a high degree of amino acid sequence homology with fibronectin, such as vitronectin (Suzuki, S., *J. Biol. Chem.*, 259:15307-15314 (1984)) can be employed in place of fibronectin. Other analogs, including analogs produced by genetic engineering techniques, can be used, provided they have cell-attaching activity of the type displayed by native-sequence fibronectin. Suitable fibronectin fragments and methods of their preparation are disclosed in U.S. Pat. No. 4,589,881, issued to Piersbacher and Ruoslahti, and U.S. Pat. No. 4,578,079, issued to Ruoslahti and Piersbacher, the disclosures of which are incorporated herein by reference. U.S. Pat. No. 4,589,881 discloses an 11.5-KDal, 108-amino acid fragment of fibronectin having cell attachment activity as well as a 30-amino acid subfragment which has cell attachment activity. U.S. Pat. No. 4,578,079 discloses fragments and analogs thereof, having the formulae X-Arg-Gly-Asp-Thr-Y, X-Arg-Gly-Asp-Cys-Y and X-Arg-Gly-Asp-Ser-Y, wherein X is H or at least one amino acid residue and Y is COOH or at least one amino acid residue. As used hereinafter, the term "fibronectin" shall be understood to include biologically active fragments and analogs thereof.

Agents which are capable of changing the pH or osmolarity of the fibronectin solution include various salts, acids, or bases which are pharmaceutically acceptable for the intended application. Examples of such compounds include mineral acids, such as hydrochloric acid, nitric acid, sulfuric acid, phosphoric acid, etc., organic acids such as acetic acid, citric acid, lactic acid, etc., bases such as sodium carbonate, sodium bicarbonate, sodium hydroxide, ammonium hydroxide, sodium phosphate, and organic bases such as tris, triethyl amine, etc., or various salts such as sodium chloride, sodium acetate, sodium sulfate, etc. Other examples of such materials which can be added to change the pH or osmolarity of aqueous solutions are well-known in the art.

Optionally, other materials which exhibit beneficial effects in wound healing, such as by providing a matrix for cell migration and growth, may also be incorporated into the gel. These are preferably proteins such as albumin or extracellular matrix (ECM) proteins. The latter are proteins which can be found in extracellular matrix structures laid down by cultured cells (Hsieh, P. and Baum, J., *Invest. Ophth. & Vis. Sci.*, 26:457-463 (1985)). They are generally high molecular weight (>150,000 daltons) fibrinous glycoproteins, which include collagens, vitronectin, elastin, laminin, actin, fibrinogen, and other ECM materials. Biologically active fragments or analogs of such proteins can also be used.

Preferably, the gel is made by reaction of a solution comprising from about 0.1 to 50 parts by weight fibronectin which usually has a pH of about 6 to 8, with an agent which can be an aqueous solution if desired such that the pH of the final fibronectin solution decreases to about 3.5 to 5. In a particularly preferred embodiment of the invention, the gel is produced by reaction of a solution comprising from about 0.1 to 50 parts by weight fibronectin which also contains from about 0.05 to 25 parts by weight albumin which usually has a pH of about 6 to 8, with an agent which can be in an aqueous solution if desired such that the pH of the final solution decreases to about 3.5 to 5.

In preparing the wound-healing dressing, the fibronectin and, optionally, other protein such as albumin is reacted with the salt or acid or base in an aqueous reaction medium or other compatible solvent system. The temperature of reaction advantageously is not great enough to cause substantial denaturation of the proteins and the reaction can be conveniently carried out at temperatures from about 15° C. to 25° C. The reaction preferably is carried out at room temperature. The reaction proceeds rapidly and is usually complete within several minutes. The reaction product appears as a flocculent in the reaction medium. The flocculent is recovered by any convenient means, such as by centrifugation, and formed into a desired shape. For example, the flocculent can be placed between two sheets of parafilm and pressed into a film of the desired thickness. The flocculent can also be placed into molds to form desired shapes. The formed gel is then air dried.

In an alternative method for preparing a wound-dressing of the invention, an aqueous solution of fibronectin and optionally, other protein such as albumin, at a concentration from about 5 mg/ml to 100 mg/ml, is poured into a thin film on a plate or other suitable surface. An aqueous solution of the salt or acid is then poured onto the film, whereupon a precipitation polymerization reaction occurs. A thin film of gel is formed which can be lifted off the plate or cut into strips and then air dried.

The dressings of the invention can be used in a variety of wound-healing applications. The precipitated fibronectin polymer exerts a number of beneficial effects on the wound-healing response. Fibronectin is a chemotactic material which induces the migration of fibroblasts or, in the case of corneal tissue, fibroblast-like cells known as keratocytes into the wound site. These cells are known to deposit a number of wound-healing substances. Furthermore, fibronectin causes the structuring of tissue in the wound bed in an organized manner, so that the healed tissue is similar in structure to normal tissue. Consequently, the undesirable effects associated with normal wound-healing processes, including scarring and contraction, may be minimized. The gel also acts as a tissue adhesive. Consequently, the wound-healing dressings of the invention can be used to provide sutureless closings for lacerations, punctures or incisions. When the wound dressings of the invention are inserted into wound openings of these types, they expand to fill in the opening between the broken tissues due to absorption of biological fluids from surrounding tissues.

If desired, the wound-healing dressings of the invention can act as carriers and delivery systems for medicaments and/or other materials which promote wound healing. For example, an antibiotic material such as gentamicin, neomycin or bacitracin can be dispersed in the gel which forms the wound healing dressing. The medicament can also be an antiviral agent, anti-inflammatory agent, hormone, vitamin, analgesic or chelating agent.

Any of the known tissue growth factors can be dispersed in the gel. Growth factors are mitogenic proteins or polypeptides which promote cell proliferation. A number of growth factors are known. These include epidermal growth factor (EGF), platelet derived growth factor (PDGF), transforming growth factors (TGF's), nerve growth factor (NGF) and others. Insulin, a polypeptide hormone, has mitogenic activity and can be used in conjunction with prostaglandin $F_{2\alpha}$, a non-peptide which has been shown to increase greatly the mitogenic activity of insulin (see Jimenez de Asua, L. et al., *Cold Spring Harbor Conf. Cell Proliferation*, Vol. 6, Sato, ed., Cold Spring Harbor Labs., New York [1979], at 403–424). Similar activation of insulin has been reported with fibroblast growth factor by Rudland, P.S. et al., *Proc. Natl. Acad. Sci., U.S.A.*, 76:1279–1293 (1974). Positive effects on cell growth have been demonstrated for platelet-derived growth factor or fibroblast-derived growth factor in combination with members of the insulin family such as somatomedins A and C (Stiles, C.D. et al, *Proc. Natl. Acad. Sci., U.S.A.*, 76:1279–1283 [1979]). Additionally, many new peptide growth factors have been isolated and characterized recently, as indicated in *Tissue Growth Factors*, R. Baserga, ed., Springer-Verlag pub., New York (1981). Antibiotics, antimicrobial agents, antiviral agents, antiimflammatory agents, anti-protease agents, hormones, vitamins, analgesics, chelating agents, mitogenic agents and mixtures thereof.

Preferred uses for the wound-healing dressings of the invention are ophthalmological applications, particularly in the treatment of corneal and scleral wounds. For example, patches cut from thin sheets of the gel can be applied as coverings over corneal wounds, including abrasions, burns, lacerations and the like, to promote wound healing. The wound-healing dressings are especially useful in enhancing the results obtainable in keratorefractive surgeries such as radial keratotomy. In one embodiment of the invention, the gel is formed into a generally wedge-shaped configuration. The wedge is inserted into the incisions made during radial keratotamy in order to fill the incision. Due to the absorption of fluid from surrounding tissue, the wedge expands to fill in the space between the incision walls. The inserted wedge acts as a spacer to prevent the incision walls from drawing together during the wound-healing process and reversing the desired corneal flattening effect of the radial keratotomy. Consequently, the amount of corneal flattening obtained upon healing of the incisions is increased. Furthermore, the fibronectin matrix causes cells to be laid down in an organized manner, i.e., in the normal "grain" of the surrounding corneal tissue. The improved organizational integrity of the healed tissue minimizes scarring and cosmetic irregularities.

Shaped plugs or wedges of the gel can also be used for sutureless closing of corneal or scleral tears or perforations, incisions or lesions. The plug or wedge is inserted into the tear, perforation, or incision where it expands to fill in the space and acts as a tissue adhesive to bind opposing edges. The gel also acts to promote wound healing within the tear or perforation. In the case of corneal perforations or scleral incisions, it may be desirable to use the gel in the configuration of a generally I-shaped cross-section. The I-shaped plug is inserted into the perforation or incision so that the longitudinal member extends through the perforation, while the opposing, parallel members rest along the anterior and posterior surfaces of the cornea. The plug swells and adheres to the interior walls of the perforation, thereby preventing fluid from leaking through the corneal perforation. If desired, the I-shaped plug may be sutured in place by suturing through the parallel members on either side of the cornea or sclera.

The following examples are intended to illustrate further the practice of the invention and are not intended to limit its scope in any way.

EXAMPLE 1

To 2.5 ml of an aqueous solution containing 14 mg/ml fibronectin and 7 mg/ml albumin was added 2 ml of 2M $Na_2SO_4$. A white flocculent slowly formed.

EXAMPLE 2

To 2.5 ml of an aqueous solution containing 14 mg/ml fibronectin and 7 mg/ml albumin was added 0.01M HCl until the pH reached about 4.5. A flocculent rapidly formed. The flocculent was removed from the aqueous solution with a stirring rod and placed between two pieces of paraffin-coated film. After 20 minutes the fibronectin-albumin film was removed from the paraffin-coated film and allowed to air dry.

EXAMPLE 3

To 3.0 ml of an aqueous solution containing 23 mg/ml fibronectin and 12.5 mg/ml albumin was added 0.01M HCl until the pH reached about 4.0. A flocculent rapidly formed. The flocculent was removed with a stirring rod and placed into a polypropylene mold in the shape of a contact lens. The mold was closed for 30 minutes. After that time, the mold was opened and the resulting gel, in the form of a contact lens was allowed to air dry. After drying, the lens was carefully removed from the mold. The resulting film was transparent and shaped like a contact lens. On being placed into water, the resulting lens became elastic, and it did not redissolve.

EXAMPLE 4

To 8.0 ml of an aqueous solution containing 8.75 mg/ml fibronectin and 4.38 mg/ml albumin was added 1.9 ml of a 0.1M acetic acid solution which had been adjusted to pH 4.4 with NaOH. The pH of the resulting solution was 4.5. A flocculent formed rapidly. The flocculent was removed from the solution with a stirring and dried as in Example 2.

EXAMPLE 5

An aqueous solution (1.0 ml) containing 50 mg/ml fibronectin and 25 mg/ml ablumin was poured onto a glass plate. Two and one half milliliters of 0.1M acetic acid solution which had been adjusted to pH 4.4 with NaOH was slowly added to the plate. A thin film formed on the bottom of the plate. After 5 minutes, the liquid was decanted from the plate. The thin film was allowed to air dry.

EXAMPLE 6

To about 0.5 ml of a solution containing about 10 mg/ml of fibronectin (no albumin) was added about 2 ml of 0.1M acetic acid solution which had been adjusted to pH 4.4 with NaOH. The pH of the resuiting solution was 4.5. A flocculent formed rapidly. The flocculent was removed with a stirring rod and placed into a polypropylene mold in the shape of a contact lens. The mold was closed for 30 minutes. After that time, the mold was opened and the resulting gel in the form of a contact lens was allowed to air dry. After drying, the lens was carefully removed from the mold. The resulting film was transparent and shaped like a contact lens. On being placed into water, the resulting lens became elastic, and it did not redissolve.

What is claimed is:

1. A method for preparing a wound-healing dressing which comprises reacting a solution containing fibronectin or a biologically active fragment or analog thereof with an agent which changes the pH or osmolarity of the solution thereby forming a flocculent; recovering the flocculent from the solution; forming the flocculent into a desired shape and drying the flocculent to thereby produce a solid, water-swellable and substantially water-insoluble wound-healing dressing.

2. The method of claim 1, wherein the agent which changes the pH or osmolarity of the solution is selected from the group consisting of a pharmaceutically acceptable mineral acid, organic acid, inorganic base, organic base or salt.

3. The method of claim 2, wherein the agent which changes the pH or osmolarity of the solution is a mineral acid and is selected from the group consisting of hydrochloric acid, nitric acid, phosphoric acid and sulfuric acid.

4. The method of claim 2, wherein the agent which changes the pH or osmolarity of the solution is an organic acid selected from the group consisting of acetic acid, citric acid, and lactic acid.

5. The method of claim 2, wherein the agent which changes the pH or osmolarity of the solution is a base selected from the group consisting of sodium carbonate, sodium bicarbonate, sodium hydroxide, ammonium hydroxide, and sodium phosphate.

6. The method of claim 2, wherein the agent which changes the pH or osmolarity of the solution is an organic base selected from the group consisting of tris(hydroxymethyl)amino methane or triethyl amine.

7. The method of claim 2, wherein the agent which changes the pH or osmolarity of the solution is a salt selected from the group consisting of sodium chloride, sodium acetate and sodium sulfate.

8. The method of claim 2, wherein a solution containing from about 0.1 to about 50 parts by weight of fibronectin is mixed with a mineral acid or an organic acid to reduce the pH of the solution to 3.5 to 5.0.

9. The method of claim 8, wherein the solution contains from about 0.05 to about 25 parts by weight albumin.

10. The method of claim 2, wherein the reaction is conducted at a temperature of from about 15° C. to about 25° C.

11. The method of claim 2, wherein the flocculent is formed into a sheet, strip, wedge or I-shaped cross-section.

12. The method of claim 1, wherein a medicament is added to the flocculent prior to forming it into a dressing.

13. The method of claim 12, wherein the medicament is an antibiotic, antimicrobial agent, antiviral agent, antiinflammatory agent, anti-protease agent, hormone, 14. The method of claim 1 wherein the solution further contains collagen.

* * * * *